US008614350B2

(12) United States Patent
Janka et al.

(10) Patent No.: US 8,614,350 B2
(45) Date of Patent: *Dec. 24, 2013

(54) CARBOXYLIC ACID PRODUCTION PROCESS EMPLOYING SOLVENT FROM ESTERIFICATION OF LIGNOCELLULOSIC MATERIAL

(75) Inventors: Mesfin Ejerssa Janka, Kingsport, TN (US); Charles Edwan Sumner, Jr., Kingsport, TN (US); Adam Scott Howard, Gray, TN (US); Kenny Randolph Parker, Afton, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/593,553

(22) Filed: Aug. 24, 2012

(65) Prior Publication Data

US 2012/0323039 A1 Dec. 20, 2012

Related U.S. Application Data

(63) Continuation-in-part of application No. 12/349,572, filed on Jan. 7, 2009, now Pat. No. 8,455,680.

(60) Provisional application No. 61/021,153, filed on Jan. 15, 2008.

(51) Int. Cl.
C07C 51/16 (2006.01)

(52) U.S. Cl.
USPC .......................... 562/412; 562/416; 562/480

(58) Field of Classification Search
None
See application file for complete search history.

(56) References Cited

U.S. PATENT DOCUMENTS

| | | | |
|---|---|---|---|
| 3,057,909 A | 10/1962 | Sebelist et al. | |
| 3,170,768 A | 2/1965 | Baldwin | |
| 3,584,039 A | 6/1971 | Meyer | |
| 3,683,018 A | 8/1972 | Longland, Jr. | |
| 3,850,983 A | 11/1974 | Park | |
| 3,931,305 A | 1/1976 | Fisher | |
| 3,996,271 A | 12/1976 | Yokota et al. | |
| 4,158,738 A | 6/1979 | Scott et al. | |
| 4,201,871 A | 5/1980 | Tanouchi et al. | |
| 4,268,690 A | 5/1981 | Komatsu et al. | |
| 4,286,101 A | 8/1981 | Hashizume et al. | |
| 4,314,073 A | 2/1982 | Crooks | |
| 4,330,676 A | 5/1982 | Moxham | |
| 4,334,086 A | 6/1982 | Hanotier et al. | |
| 4,356,319 A | 10/1982 | Roffia et al. | |
| 4,357,475 A | 11/1982 | Hanotier et al. | |
| 4,447,646 A | 5/1984 | Johnson et al. | |
| 4,500,732 A | 2/1985 | Petty-Weeks et al. | |
| 4,588,414 A | 5/1986 | Takegami et al. | |
| 4,605,763 A | 8/1986 | Kiefer et al. | |
| 4,707,274 A | 11/1987 | Donhauser et al. | |
| 4,804,384 A * | 2/1989 | Rowell et al. | 8/121 |
| 4,812,233 A | 3/1989 | Coenen et al. | |
| 4,861,919 A | 8/1989 | Robbins et al. | |
| 4,939,297 A | 7/1990 | Browder et al. | |
| 5,008,450 A | 4/1991 | Yamamoto et al. | |
| 5,080,721 A | 1/1992 | Flanigan et al. | |
| 5,095,146 A | 3/1992 | Zeitlin et al. | |
| 5,107,874 A | 4/1992 | Flanigan et al. | |
| 5,116,423 A | 5/1992 | Kokkonen et al. | |
| 5,143,554 A | 9/1992 | Koyama et al. | |
| 5,175,355 A | 12/1992 | Streich et al. | |
| 5,200,557 A | 4/1993 | Gee et al. | |
| 5,359,133 A | 10/1994 | Nazimok et al. | |
| 5,454,959 A | 10/1995 | Stevens | |
| 5,527,957 A | 6/1996 | Hindmarsh et al. | |
| 5,563,293 A | 10/1996 | Hindmarsh et al. | |
| 5,567,842 A | 10/1996 | Izumisawa et al. | |
| 5,583,254 A | 12/1996 | Turner et al. | |
| 5,616,792 A | 4/1997 | Bartos et al. | |
| 5,635,074 A | 6/1997 | Stenstrom et al. | |
| 5,643,468 A | 7/1997 | Ure | |
| 5,676,847 A | 10/1997 | Yamamoto et al. | |
| 5,679,846 A | 10/1997 | Hindmarsh et al. | |
| 5,684,187 A | 11/1997 | Ohkoshi et al. | |
| 5,686,638 A | 11/1997 | Kos et al. | |
| 5,698,734 A | 12/1997 | Turner et al. | |
| 5,712,412 A | 1/1998 | Inary et al. | |
| 5,723,656 A | 3/1998 | Abrams | |
| 5,756,833 A | 5/1998 | Rosen et al. | |
| 5,763,649 A | 6/1998 | Fukuhara | |
| 5,777,101 A | 7/1998 | Nelson et al. | |
| 5,777,161 A | 7/1998 | Inary | |

(Continued)

FOREIGN PATENT DOCUMENTS

| | | |
|---|---|---|
| DE | 3128474 | 6/1982 |
| EP | 0111784 | 2/1986 |

(Continued)

OTHER PUBLICATIONS

USPTO Notice of Allowance dated Apr. 11, 2013 for co-pending U.S. Appl. No. 12/349,572.

Arun Pal Aneja and Viney Pal Aneja, "The Effect of Water and Air Contamination on Poly (Ethylene Terephthalate) Formation", *Polymer Engineering Reviews*, 1982, pp. 123-133, vol. 2, No. 2.

M.Maties, R. Bacai Oglu, R.F. Paie & H.H. Glatt, "Study of Di- and Polyesterification, I. Esterification of Ethylene and Diethylene Glycols with Acetic Acid," (1978), Chemical Bulletin of the Technical University of Timisoara, 23 (37), pp. 73-76.

(Continued)

*Primary Examiner* — Sudhakar Katakam
(74) *Attorney, Agent, or Firm* — Steven A. Owen

(57) ABSTRACT

Methods and apparatus for producing a carboxylic acid employing a solvent from esterification of lignocellulosic materials. An acid-containing composition from esterification of lignocellulosic materials can be employed in the oxidation of para-xylene to terephthalic acid. The acid-containing composition can comprise acetic acid, acetic anhydride, and one or more terpenes or terpenes derivatives.

25 Claims, 3 Drawing Sheets

(56) References Cited

U.S. PATENT DOCUMENTS

Figure 1:
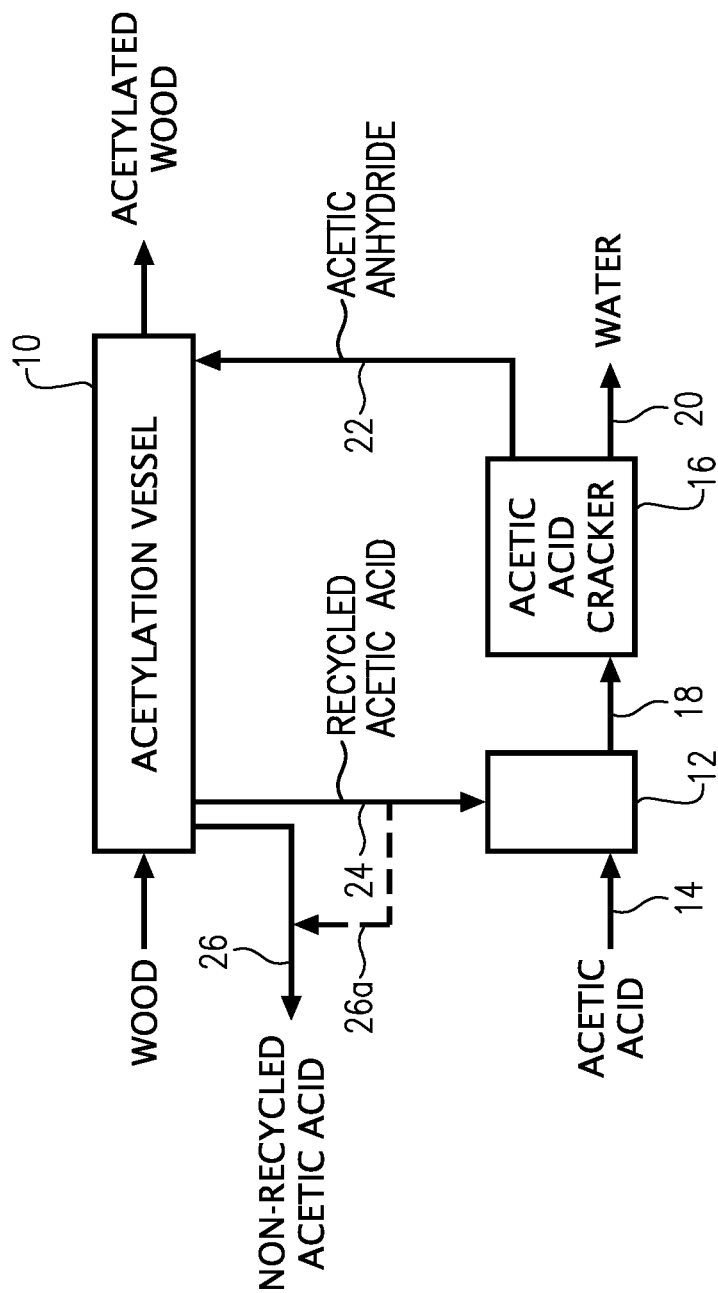

| | | |
|---|---|---|
| 5,840,965 A | 11/1998 | Turner et al. |
| 5,840,968 A | 11/1998 | Lee et al. |
| 5,916,422 A | 6/1999 | Kimura et al. |
| 5,925,786 A | 7/1999 | Isayama et al. |
| 5,955,394 A | 9/1999 | Kelly |
| 6,037,491 A | 3/2000 | Vassiliou et al. |
| 6,228,215 B1 | 5/2001 | Hoffman, Jr. |
| 6,297,348 B1 | 10/2001 | Rodden et al. |
| 6,307,099 B1 | 10/2001 | Turner et al. |
| 6,476,257 B1 * | 11/2002 | Park et al. .................. 562/412 |
| 6,495,044 B1 | 12/2002 | Verdoes |
| 6,517,733 B1 | 2/2003 | Carlson |
| 6,562,997 B2 | 5/2003 | Sikkenga et al. |
| 6,700,030 B2 | 3/2004 | Schweitzer et al. |
| 6,797,073 B1 | 9/2004 | Teruggi et al. |
| 7,048,835 B2 | 5/2006 | Jang et al. |
| 7,612,232 B2 | 11/2009 | Warner et al. |
| 7,790,922 B2 | 9/2010 | Warner et al. |
| 7,960,581 B2 | 6/2011 | De Vreede et al. |
| 8,455,680 B2 * | 6/2013 | Fornara et al. ............... 562/412 |
| 2002/0193630 A1 | 12/2002 | Lin et al. |
| 2003/0004372 A1 | 1/2003 | Piras et al. |
| 2004/0245176 A1 | 12/2004 | Parker et al. |
| 2004/0260052 A1 | 12/2004 | Nagao et al. |
| 2005/0087215 A1 | 4/2005 | Miyahara et al. |
| 2009/0234157 A1 | 9/2009 | Warner et al. |
| 2009/0247788 A1 | 10/2009 | Warner et al. |

FOREIGN PATENT DOCUMENTS

| | | |
|---|---|---|
| EP | 0213252 | 3/1987 |
| FR | 1098768 | 8/1955 |
| GB | 983677 | 2/1965 |
| GB | 1152577 | 5/1969 |
| GB | 1260755 | 1/1972 |
| GB | 1358520 | 7/1974 |
| GB | 1388289 | 3/1975 |
| JP | 48-26740 | 9/1973 |
| JP | 7-149690 | 6/1995 |
| JP | 7-291896 | 11/1995 |
| JP | 9-286758 | 11/1997 |
| JP | 9-286759 | 11/1997 |
| JP | 2001-139514 | 5/2001 |
| JP | 2001-247511 | 9/2001 |
| JP | 2001-288139 | 10/2001 |
| JP | 2002-230819 | 8/2002 |
| JP | 2003-128624 A | 5/2003 |
| WO | WO 93/24440 | 12/1993 |
| WO | WO 94/17892 | 8/1994 |
| WO | WO 98/38150 A1 | 9/1998 |
| WO | WO 99/31038 A1 | 6/1999 |

OTHER PUBLICATIONS

Notification of Transmittal of the International Search Report for PCT International Application No. PCT/US2009/000168 with Date of Mailing Jun. 5, 2009.

* cited by examiner

CARBOXYLIC ACID PRODUCTION PROCESS EMPLOYING SOLVENT FROM ESTERIFICATION OF LIGNOCELLULOSIC MATERIAL

RELATED APPLICATIONS

This application is a Continuation-In-Part of U.S. application Ser. No. 12/349,572, filed Jan. 7, 2009, titled "CARBOXYLIC ACID PRODUCTION PROCESS EMPLOYING SOLVENT FROM ESTERIFICATION OF LIGNOCELLULOSIC MATERIAL", which claims priority to U.S. Provisional Application Ser. No. 61/021,153, filed Jan. 15, 2008, titled "CARBOXYLIC ACID PRODUCTION PROCESS EMPLOYING SOLVENT FROM ESTERIFICATION OF LIGNOCELLULOSIC MATERIAL," both prior applications are hereby incorporated by reference in their entirety to the extent that they do not contradict statements herein.

BACKGROUND OF THE INVENTION

1. Field of the Invention

The present invention relates generally to carboxylic acid production processes. More specifically, the present invention concerns equipment and processes for producing carboxylic acids employing solvent originating from a process involving esterification of lignocellulosic material.

2. Description of the Prior Art

In conventional terephthalic acid ("TPA") production processes, para-xylene undergoes oxidation to form crude terephthalic acid ("CTA") particles. A slurry of CTA particles can then undergo purification to form purified terephthalic acid ("PTA") particles. A purified slurry comprising PTA particles and a liquid phase can then be treated in a product isolation zone to isolate at least a portion of the PTA particles. During the TPA production process, a solvent is typically introduced into the oxidizer along with the para-xylene. Additionally, solvent can be added during the purification step to replenish solvent lost during the oxidation process due to decarboxylation. This solvent initially acts as a carrier fluid for the para-xylene, and later as a carrier fluid for the TPA formed in the oxidation reactor. Though these processes are generally known in the art, given its high global demand improved production processes for TPA are continually needed.

In another process, lignocellulosic material (e.g., wood) can undergo esterification (e.g., acetylation) for purposes of, inter alia, making the lignocellulosic material more dimensionally stable, more weather resistant, and/or insect resistant. In a typical lignocellulosic material esterification process, the lignocellulosic material is contacted with a compound containing an acetyl group, such as acetic anhydride. The hydroxyl groups in the lignocellulosic material can then react with acetyl groups from the anhydride, thus forming acetylated lignocellulosic material and an acid-containing composition. When acetic anhydride is employed in this process, acetic acid is produced as a byproduct. A portion of the acetic acid can be recycled in order to form more anhydride by, for example, a cracking process and reaction with ketene. However, at least a portion of the acid can be removed from the process in order to control the level of impurities, such as, for example, terpenes.

SUMMARY OF THE INVENTION

In one embodiment of the present invention, there is provided a process for producing a carboxylic acid. The process of this embodiment comprises oxidizing an oxidation feed comprising at least one oxidizable compound and at least one solvent comprising a monocarboxylic acid, where at least a portion of the monocarboxylic acid originated from a wood acetylation process.

In another embodiment of the present invention, there is provided a process for producing a carboxylic acid. The process of this embodiment comprises (a) contacting at least one lignocellulosic material with a compound containing at least one acetyl group to thereby produce an acetylated lignocellulosic material and an acid-containing composition; and (b) introducing at least a portion of the acid-containing composition and an oxidizable compound into a carboxylic acid production process, where the acid-containing composition comprises acetic acid.

In yet another embodiment of the present invention, there is provided a process for producing a carboxylic acid. The process of this embodiment comprises oxidizing an oxidizable compound in an oxidation reactor in the presence of at least one solvent. The solvent comprises acetic anhydride in an amount of at least 0.01 weight percent based on the total weight of the solvent.

BRIEF DESCRIPTION OF THE DRAWING FIGURES

Figure 2:
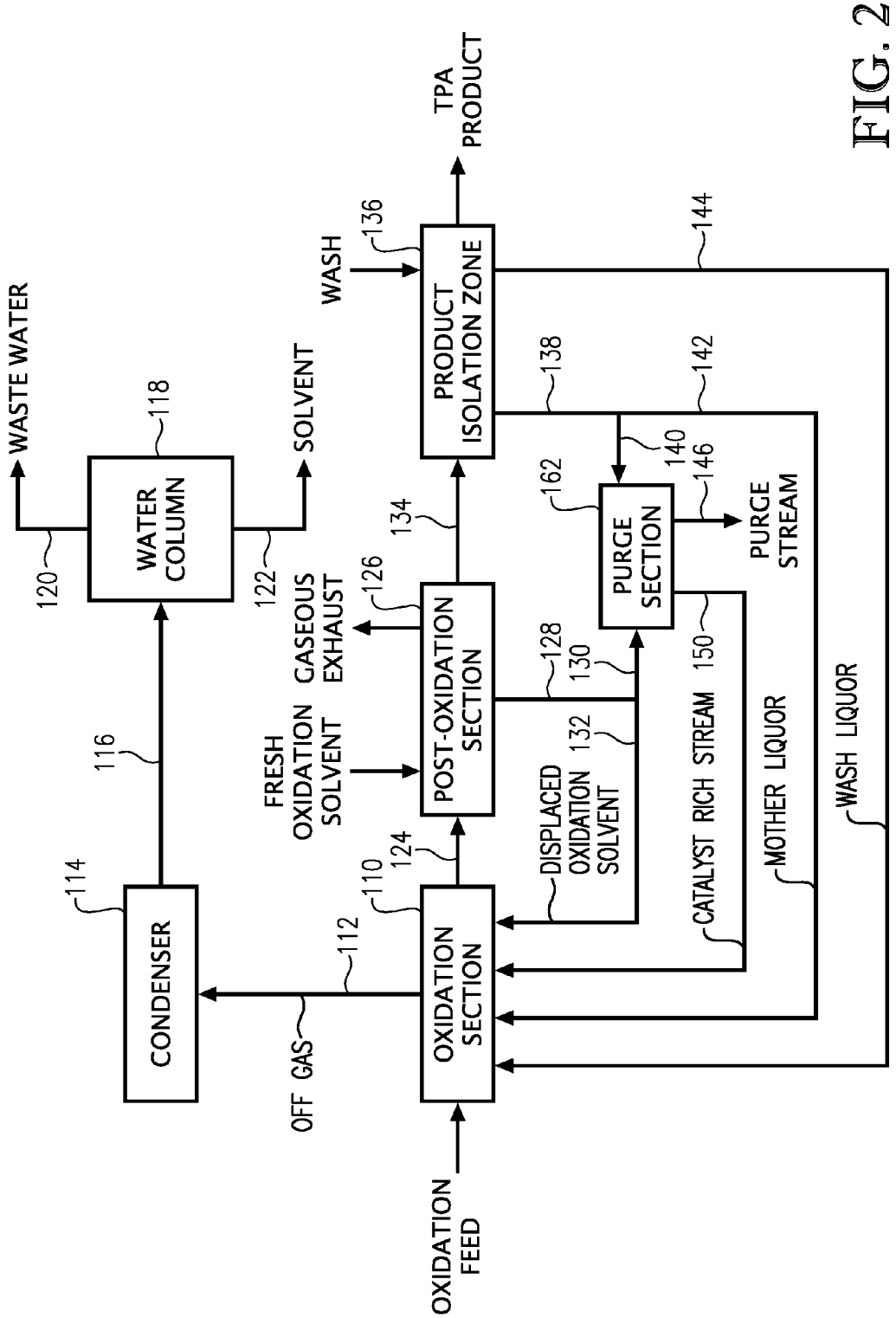

A preferred embodiment of the present invention is described in detail below with reference to the attached drawing figures, wherein:

FIG. 1 is a process flow diagram of a wood acetylation process, particularly illustrating a configuration where acetic acid is cracked to form acetic anhydride and water, and acetic anhydride is routed to an acetylation reactor for acetylating wood; and FIG. 2 is a process flow diagram illustrating a system for the production and purification of carboxylic acid constructed in accordance with the present invention, particularly illustrating a configuration where the crude slurry from the oxidation reactor is subjected to purification, the resulting purified slurry is subjected to product isolation, and a portion of the mother liquor from the product isolation zone is employed as a feed to a purge treatment system.

Figure 3:
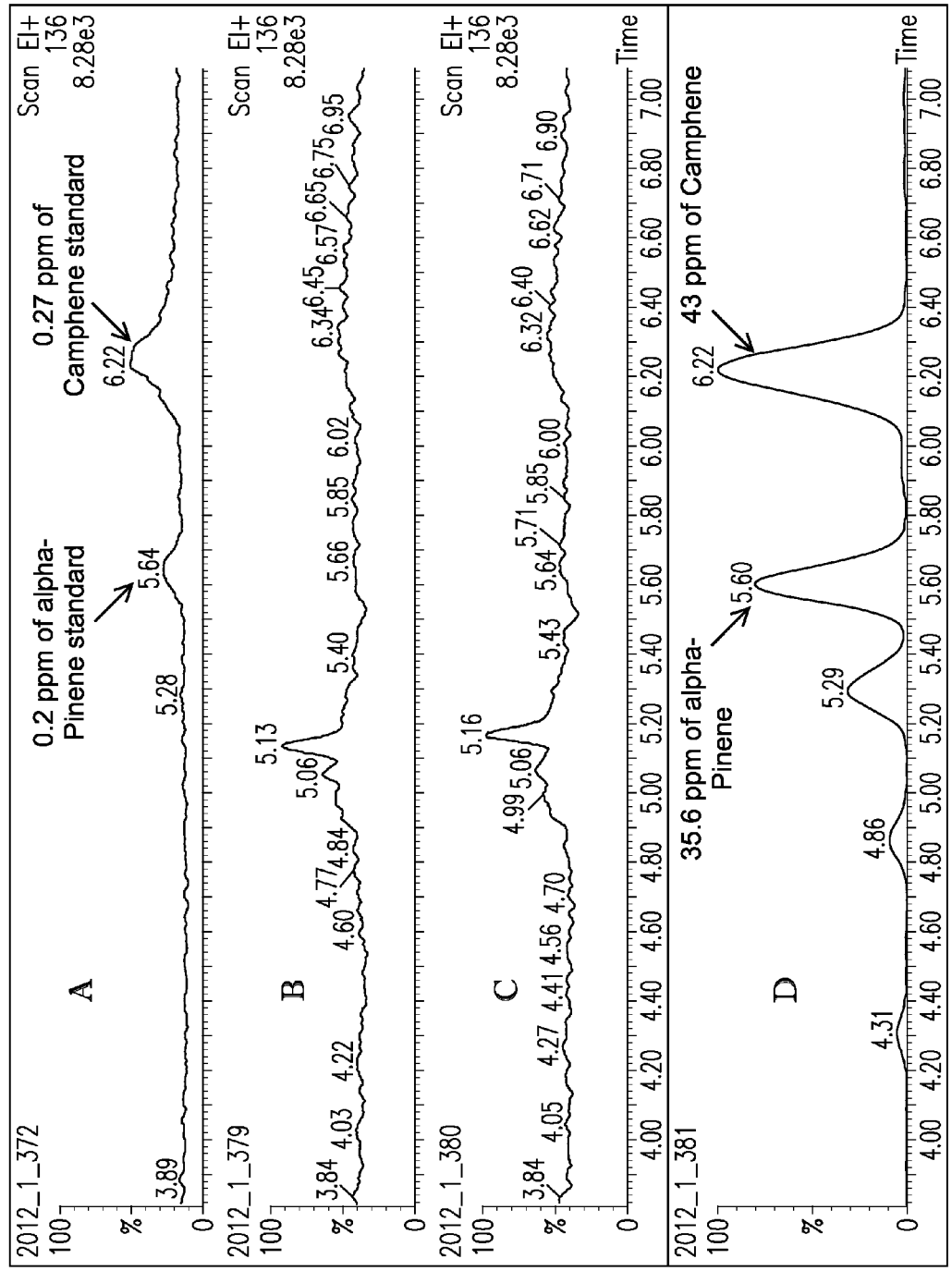

FIG. 3 is Mass Selective GC Chromatogram of: (A) Alpha-Pinene and Camphene standards. (B) Filtrate sample from p-xylene (pX) oxidation using acetic acid solvent recovered from wood acetylation process. (C) Trap sample from p-xylene (pX) oxidation using acetic acid solvent recovered from wood acetylation process. And (D) acetic acid solvent recovered from wood acetylation process.

DETAILED DESCRIPTION

In accordance with one embodiment of the present invention, a lignocellulosic material (e.g., wood) can undergo an esterification (e.g., acetylation) process to produce an esterified lignocellulosic material (e.g., acetylated wood) and an acid-containing composition. At least a portion of this acid-containing composition can be employed in a process for producing carboxylic acid (e.g., terephthalic acid ("TPA")).

The above-mentioned esterification process employed in the present invention can be any known esterification process for generating an esterified lignocellulosic material and an acid-containing composition. In one embodiment, the esterification process can be any known process for producing acetylated wood. As used herein, the term "acetylated" shall denote a substance that has been chemically altered to contain one or more acetyl groups. In general, an esterification process of the present invention can include contacting a lignocellulosic material with an impregnating compound capable of esterifying the lignocellulosic material. As will be discussed in further detail below, the esterification can be performed under pressure and/or under conditions of increased temperature. Furthermore, the esterification can be performed in a suitable reaction vessel.

The lignocellulosic material in the above-mentioned esterification process can be any lignocellulosic material capable of being esterified. As used herein, the term "lignocellulosic" shall denote any material that contains lignin along with cellulose and/or hemicellulose.

In one embodiment, the lignocellulosic material suitable for use in the present invention can be wood. When wood is employed as the lignocellulosic material, the form of the wood suitable for use in the present invention is not limited and can be employed in any dimension or shape. In one embodiment, the wood can be in the form of veneers, boards, planks, squared timber, beams or profiles, wood particles, wood flakes, or wooden end products. When wood particles are employed, the wood scrap can be in the form of wood flour, wood fibers, and wood shavings obtained from wood processing. Mixtures of wood scraps can also be used. Additionally, the species of wood is not critical, as any species of wood can be employed in the present invention. In one embodiment, the wood employed in the present invention can comprise broad-leaved or coniferous wood (generally speaking, hard or soft woods respectively).

The lignocellulosic material suitable for use in the above-mentioned esterification process can contain water. In one embodiment, the lignocellulosic material can initially contain at least about 15 weight percent water, at least about 17 weight percent water, or at least 19 weight percent water prior to esterification. In one embodiment, the lignocellulosic material can be dewatered to produce a dewatered lignocellulosic material having a water content of less than about 15 weight percent water, less than about 10 weight percent water, or less than 5 weight percent water. Any method known in the art can be employed to achieve the desired water content of the lignocellulosic material prior to esterification. In one embodiment, kiln drying and/or drying by acetic acid impregnation coupled with vacuum/pressure cycles can be employed to achieve the desired water content.

The impregnating compound of the present invention can be any compound capable of reacting with one or more hydroxyl groups in the lignocellulosic material to thereby form an esterified lignocellulosic material and an acid-containing composition. In one embodiment, the impregnating compound can be an anhydride. Examples of anhydrides suitable for use in the present invention include, but are not limited to, acetic anhydride, propionic anhydride, butyric anhydride, pentanoic anhydride, hexanoic anhydride, and their isomers, as well as any mixed anhydrides containing acetic, propionic, butyric, pentanoic, and/or hexanoic moieties and their isomers. In one embodiment, the impregnating compound can predominately comprise acetic anhydride. As used herein, the terms "majority," "primarily," and "predominately" shall mean more than 50 percent. In another embodiment, the impregnating compound can comprise acetic anhydride in an amount of at least about 70, at least about 80, or at least 95 weight percent.

In one embodiment, the impregnating compound can be employed in the present invention as substantially the sole reagent. In another embodiment, the impregnating compound can be used in combination with other compounds, such as, for example, tertiary amines, acetone, pyridine, aromatic hydrocarbons, and/or chlorinated hydrocarbons. Furthermore, the impregnating compound can comprise acetic acid. Additionally, one or more catalysts can be employed in the esterification of the lignocellulosic material.

The amount of impregnating compound employed can be any amount sufficient to increase the total acetyl content of the starting lignocellulosic material by at least 1 weight percent, at least 2 weight percent, or at least 3 weight percent, based on the total weight of the lignocellulosic material. The total acetyl content of the lignocellulosic material can be determined according to the saponification method, as is known in the art. In one embodiment, the amount of impregnating compound absorbed by the lignocellulosic material can be in the range of from about 50 to about 250 weight percent, in the range of from about 65 to about 200 weight percent, or in the range of from 80 to 150 weight percent, based on the weight of the dewatered wood.

As mentioned above, the esterification process employed in the present invention can be performed at elevated pressure and/or temperature. The pressure and temperature employed in the present invention can be any pressure and temperature suitable to increase the total acetyl content of the starting lignocellulosic material by at least 1 weight percent, at least 2 weight percent, or at least 3 weight percent, based on the total weight of the lignocellulosic material. In one embodiment, the esterification can be performed at temperatures of at least about 40° C., at least about 65° C., or at least 90° C. Additionally, the esterification can be performed at a pressure of at least about 20 pounds per square inch gauge (psig), in the range of from about 25 to about 150 psig, in the range of from about 35 to about 125 psig, or in the range of from 50 to 100 psig.

The acid-containing composition originating in the esterification process can vary depending on the chosen impregnating compound. The acid-containing composition of the present invention can comprise any acid derivative of the above-described impregnating compounds. In one embodiment, the acid-containing composition can comprise an organic low molecular weight monocarboxylic acid having from 1 to 6 carbon atoms. For example, the acid-containing composition can comprise acetic acid, propionic acid, butyric acid, pentanoic acid, and/or hexanoic acid. In one embodiment, the acid-containing composition predominately comprises acetic acid. In another embodiment, the acid-containing composition can comprise acetic acid in an amount of at least about 70, at least about 80, or at least 95 weight percent.

Following esterification, the esterified lignocellulosic material can be subject to a drying process so as to remove any excess impregnating compound and residual acid remaining in the lignocellulosic material. In one embodiment, the drying process can be performed in the same reaction vessel as the esterification step. The drying process can be any drying process known in the art capable of lowering the free acid content of the esterified lignocellulosic material to any desired level. Examples of drying processes that can be employed in the present invention include, but are not limited to, application of heat with inert gas (e.g., nitrogen) flow, addition of steam to the reaction vessel, addition of water to the reaction vessel, or drying in a kiln which can be equipped to collect any acid removed via condensation.

FIG. 1 illustrates an example of a lignocellulosic material esterification process suitable for use in the present invention. In particular, FIG. 1 depicts a wood acetylation process where wood can be inserted into an acetylation vessel 10. Fresh acetic acid can be introduced into holding tank 12 via line 14. In one embodiment, the fresh acetic acid can be glacial acetic acid. As used herein, the term "glacial acetic acid" denotes acetic acid having a purity of at least 99.8 percent by weight.

As will be discussed in more detail below, the fresh acetic acid in holding tank 12 can be combined with recycled acetic acid from acetylation vessel 10. Once combined, at least a portion of the acetic acid can be routed to cracking vessel 16 via line 18.

In cracking vessel 16, at least a portion of the acetic acid can be cracked to produce water and an intermediate ketene; thereafter, the acetic acid and ketene react to form acetic anhydride. In one embodiment, at least about 50, at least about 70, or at least 90 weight percent of the acetic acid introduced into cracking vessel 16 is cracked to eventually form water and acetic anhydride. Cracking of the acetic acid in cracking vessel 16 can be accomplished by any cracking methods known in the art that are capable of cracking acetic acid to eventually form acetic anhydride and water. For example, cracking of the acetic acid can be accomplished by thermal cracking and/or by chemical cracking, such as, for example, catalytic cracking. In another embodiment, the acetic acid can be subject to any ketene process known in the art suitable for converting acetic acid into acetic anhydride. Additionally, it should be noted that the acetic anhydride useful in the present invention is not limited by the method of its production, as acetic anhydride produced by any method can be used in the process of the present invention.

Water produced from the cracking process can be routed out of cracking vessel 16 via line 20. Acetic anhydride produced in cracking vessel 16 can be routed to acetylation vessel 10 via line 22. It should be noted, however, that acetic anhydride useful in the esterification process of the present invention is not limited to that produced in an adjoining cracking vessel, and may originate from any available source of acetic anhydride. Furthermore, it should be noted that the acetylating reagent is not limited to acetic anhydride, as any acetylating reagent can be employed in the present invention. Once in acetylation vessel 10, the acetic anhydride acts to acetylate the wood according to the following reaction:

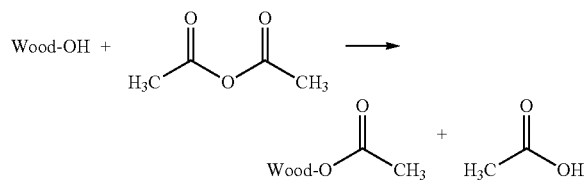

As the foregoing equation illustrates, the acetylation of wood with acetic anhydride produces acetylated wood and acetic acid as a byproduct. In one embodiment, at least a portion of the acetic acid produced during the acetylation process can be recycled back to holding tank 12 via line 24, where it can be combined with fresh acetic acid introduced via line 14. Thus, at least a portion of the acetic acid byproduct can be continually reused.

However, a portion of the acetic acid originating in the above process can be removed from acetylation vessel 10. This prevents contaminants drawn from the wood from building up in the cycle depicted in FIG. 1. For example, terpenes or terpenes derivatives from the wood can become entrained with the acetic acid resulting from acetylation. Accordingly, at least a portion of the acid-containing composition can be removed from the system as non-recycled acid-containing composition. The non-recycled acid-containing composition can be withdrawn from acetylation vessel 10 via line 26. Alternatively, the non-recycled acid-containing composition can be withdrawn from line 24 via line 26a. It should be noted, however, that the location where the non-recycled acid-containing composition is withdrawn is not critical, and can originate from any portion of the acetylation process. The amount of acid-containing composition withdrawn via line 26 and/or line 26a can be in the range of from about 0.01 to about 25 weight percent, in the range of from about 0.05 to about 15 weight percent, or in the range of from 0.1 to 5 weight percent of the total amount of acid-containing composition withdrawn from acetylation vessel 10.

As mentioned above, at least a portion of the acid-containing composition originating from esterification of a lignocellulosic material can be employed in a process for making carboxylic acids. Any carboxylic acid production process that involves oxidizing an oxidizable compound in the presence of a solvent can be employed in the present invention. As used herein, a "carboxylic acid production process" and a "TPA production process" are defined as beginning with an initial oxidation step and ending with a carboxylic acid product, and can, but need not necessarily, include therein one or more purification steps, concentration steps, isolation steps, purge steps, and/or additional oxidation steps.

FIG. 2 illustrates a carboxylic acid production process suitable for use in the present invention. In the embodiment illustrated in FIG. 2, a predominately fluid-phase feed stream containing an oxidizable compound (e.g., para-xylene), a solvent (e.g., acetic acid and/or water), and a catalyst system (e.g., cobalt, manganese, and/or bromine) can be introduced into oxidation zone 110. A predominately gas-phase oxidant stream containing molecular oxygen can also be introduced into oxidation zone 110. The fluid- and gas-phase feed streams form a multi-phase reaction medium in oxidation zone 110. The oxidizable compound can undergo partial oxidation in a liquid phase of the reaction medium contained in oxidation zone 110.

In one embodiment of the present invention, oxidation zone 110 can comprise an agitated reactor. Agitation of the reaction medium in oxidation zone 110 can be provided by any means known in the art. As used herein, the term "agitation" shall denote work dissipated into the reaction medium causing fluid flow and/or mixing. In one embodiment, oxidation zone 110 can be a mechanically-agitated reactor equipped with means for mechanically agitating the reaction medium. As used herein, the term "mechanical agitation" shall denote agitation of the reaction medium caused by physical movement of a rigid or flexible element(s) against or within the reaction medium. For example, mechanical agitation can be provided by rotation, oscillation, and/or vibration of internal stirrers, paddles, vibrators, or acoustical diaphragms located in the reaction medium. In another embodiment of the present invention, oxidation zone 110 can comprise a bubble column reactor. As used herein, the term "bubble column reactor" shall denote a reactor for facilitating chemical reactions in a multi-phase reaction medium, wherein agitation of the reaction medium is provided primarily by the upward movement of gas bubbles through the reaction medium.

The oxidizable compound present in the fluid-phase feed stream introduced into oxidation zone 110 can comprise at least one hydrocarbyl group. Also, the oxidizable compound can comprise an aromatic compound. In one embodiment, the oxidizable compound can comprise an aromatic compound with at least one attached hydrocarbyl group or at least one attached substituted hydrocarbyl group or at least one attached heteroatom or at least one attached carboxylic acid function (—COOH). In another embodiment, the oxidizable compound can comprise an aromatic compound with at least one attached hydrocarbyl group or at least one attached substituted hydrocarbyl group with each attached group comprising from 1 to 5 carbon atoms. In yet another embodiment, the oxidizable compound can be an aromatic compound having exactly two attached groups with each attached group comprising exactly one carbon atom and consisting of methyl groups and/or substituted methyl groups and/or at most one carboxylic acid group. Suitable examples of the oxidizable compound include, but are not limited to, para-xylene, meta-xylene, para-tolualdehyde, meta-tolualdehyde, para-toluic acid, meta-toluic acid, and/or acetaldehyde. In one embodiment of the present invention, the oxidizable compound comprises para-xylene.

A "hydrocarbyl group," as defined herein, is at least one carbon atom that is bonded only to hydrogen atoms and/or to other carbon atoms. A "substituted hydrocarbyl group," as defined herein, is at least one carbon atom bonded to at least one heteroatom and to at least one hydrogen atom. "Heteroatoms," as defined herein, are all atoms other than carbon and hydrogen atoms. "Aromatic compounds," as defined herein, comprise an aromatic ring and can comprise at least 6 carbon atoms and can also comprise only carbon atoms as part of the ring. Suitable examples of such aromatic rings include, but are not limited to, benzene, biphenyl, terphenyl, naphthalene, and other carbon-based fused aromatic rings.

The amount of oxidizable compound present in the fluid-phase feed stream introduced into oxidation zone 110 can be in the range of from about 4 to about 20 weight percent, or in the range of from 6 to 15 weight percent.

The solvent present in the fluid-phase feed stream introduced into oxidation zone 110 can comprise an acid component and a water component. The solvent can be present in the fluid-phase feed stream at a concentration in the range of from about 60 to about 98 weight percent, in the range of from about 80 to about 96 weight percent, or in the range of from 85 to 94 weight percent. The acid component of the solvent can be an organic low molecular weight monocarboxylic acid having from 1 to 6 carbon atoms, or 2 carbon atoms. In one embodiment, the acid component of the solvent can comprise acetic acid. The acid component can make up at least about 75 weight percent of the solvent, at least about 80 weight percent of the solvent, or in the range of from 85 to 98 weight percent of the solvent, with the balance being primarily water.

In one embodiment of the present invention, at least a portion of the solvent present in the fluid-phase feed stream introduced into oxidation zone 110 can comprise an acid-containing composition originating from esterification of a lignocellulosic material, as described above. Furthermore, either additionally or alternatively, an acid-containing composition can be introduced into oxidation zone 110 as a separate feed stream (not depicted). As mentioned above, the acid-containing composition can comprise acetic acid. In addition, the acid-containing composition suitable for use in a carboxylic acid production process can comprise acetic anhydride and/or one or more terpenes or terpenes derivatives. In one embodiment, the acid-containing composition can comprise acetic anhydride in an amount of at least about 0.01 weight percent, at least about 0.05 weight percent, or at least 0.1 weight percent based on the weight of the acid in the acid-containing composition. Additionally, the acid-containing composition can comprise terpenes or terpenes derivatives in a combined amount of at least about 0.01 weight percent, at least about 0.04 weight percent, or at least 0.08 weight percent based on the weight of the acid in the acid-containing composition. Furthermore, the one or more terpenes in the acid-containing composition can comprise of limonene, or pinene.

Though not wishing to be bound by theory, it is believed that the presence of acetic anhydride in the solvent employed during oxidation will consume some of the water produced in the oxidation process. This is because water readily reacts with acetic anhydride to form acetic acid. As depicted in FIG. 2, ordinarily water is removed from oxidation zone 110 along with the off gas via line 112 in the form of vapor. Off gas in line 112 can have a water content of at least about 4 weight percent, at least about 8 weight percent, or at least 12 weight percent.

The off gas in line 112 can first be treated in condenser 114 to thereby form a condensed off gas being predominately in liquid phase. The condensed off gas can then be routed to water column 118 via line 116. In water column 118, the water can be separated from other solvents removed with the off gas. Solvent separated from the condensed off gas in water column 118 can be removed via line 122. The solvent in line 122 can be substantially comprised of acetic acid. The separated water can be removed as waste water from water column 118 via line 120 and or used elsewhere in the process. Generally, the waste water in line 120 can have a water content of at least about 85 weight percent, at least about 95 weight percent, or at least 99 weight percent.

In one embodiment, though not depicted, energy can be recovered from the waste water in line 120, which can at least partially be in the form of steam. In one embodiment, the waste water in line 120 can have a temperature in the range of from about 100 to about 175° C., in the range of from about 115 to about 160° C., or in the range of from 130 to 145° C. Additionally, the waste water in line 120 can have a pressure in the range of from about 60 to about 120 pounds per square inch absolute (psia), or in the range of from 80 to 100 psia.

Any known method in the art suitable for converting at least a portion of the energy of steam into work can be employed for energy recovery in the present invention. In one embodiment, energy can be recovered from the waste water in line 120 by introducing at least a portion of the waste water into a turboexpander (not depicted), which can convert at least a portion of the energy of the waste water into work. In another embodiment, energy can be recovered by employing at least a portion of the waste water in line 120 to heat the working fluid in an organic Rankine cycle (not depicted). In another embodiment, energy may be recovered from at least a portion of the hot non-condensable gas contained in off gas stream 112. Hot non-condensable gas can be isolated in the condenser zone 114 and or the water column zone 118 and then routed to an energy recovery system. Any known method in the art suitable for converting at least a portion of the energy contained in the non-condensable hot gas into work can be employed for energy recovery in the present invention. In one embodiment, energy can be recovered from the non-condensable hot gas isolated in the condenser zone 114 and or the water column zone 118 by introducing at least a portion of the hot non condensable gas into a turbo expander (not depicted), which can convert at least a portion of the energy contained in the non-condensable hot gas isolated in the condenser zone 114 and or the water column zone 118 of the waste water into work. In another embodiment, energy can be recovered by employing at least a portion of the energy in the non-condensable hot gas isolated in the condenser zone 114 and or the water column zone 118 to heat the working fluid in an organic Rankine cycle (not depicted).

The above-described process of removing water and treating the off gas from oxidation zone 110 can be time consuming and costly. The process, though, could be done more quickly and with lower cost if less water had to be withdrawn from oxidation zone 110. As mentioned above, it is believed that the residual acetic anhydride in the acid-containing composition from the esterification of a lignocellulosic material can accomplish this task by consuming some of the water produced during oxidation. Accordingly, the use of an acid-containing composition from a lignocellulosic material esterification process has the unexpected benefit of lowering production costs associated with a carboxylic acid production process. In one embodiment, at least about 10 weight percent, at least about 50 weight percent, or at least 90 weight percent of the acetic anhydride in the solvent reacts with water in oxidation zone 110 to produce an acid.

Another unexpected result of employing an acid-containing composition from the esterification of a lignocellulosic material concerns the presence of terpenes or terpenes derivatives. Ordinarily, the presence of terpenes or terpenes derivatives renders a solvent unsuitable for use in processes that may typically employ an acid-containing solvent (e.g., a solvent containing acetic acid). This is because such processes usually cause the terpenes or terpenes derivatives to convert into tar or other substances that can foul equipment being employed in these processes. However, in the current invention, the inventors have discovered that terpenes or terpenes derivatives tend to be oxidized in the process employed, thus typically forming carbon monoxide and carbon dioxide. See FIG. 3 for Mass Selective Chromatograms before and after oxidation and summary Table 1. Accordingly, the presence of terpenes or terpenes derivatives in a carboxylic acid production process is not believed to have a negative operational impact on the equipment employed as well as to conversion and yield, Tables 2, 3 and 4. Thus, while an acid-containing composition from the esterification of a lignocellulosic material may not be suitable in many other processes, it is unexpectedly suited for use as at least a portion of the solvent employed in a carboxylic acid production process. In an embodiment of the invention, at least 70, or at least 90, or at least 99, or at least 99.9 weight percent of the terpenes or terpenes derivatives is oxidized in the oxidation zone 110.

As mentioned above, the fluid-phase feed stream introduced into oxidation zone 110 can also include a catalyst system. The catalyst system can be a homogeneous, liquid-phase catalyst system capable of promoting at least partial oxidation of the oxidizable compound. Also, the catalyst system can comprise at least one multivalent transition metal. In one embodiment, the catalyst system can comprise cobalt, bromine, and/or manganese.

When cobalt is present in the catalyst system, the fluid-phase feed stream can comprise cobalt in an amount such that the concentration of cobalt in the liquid phase of the reaction medium is maintained in the range of from about 300 to about 6,000 parts per million by weight (ppmw), in the range of from about 700 to about 4,200 ppmw, or in the range of from 1,200 to 3,000 ppmw. When bromine is present in the catalyst system, the fluid-phase feed stream can comprise bromine in an amount such that the concentration of bromine in the liquid phase of the reaction medium is maintained in the range of from about 300 to about 5,000 ppmw, in the range of from about 600 to about 4,000 ppmw, or in the range of from 900 to 3,000 ppmw. When manganese is present in the catalyst system, the fluid-phase feed stream can comprise manganese in an amount such that the concentration of manganese in the liquid phase of the reaction medium is maintained in the range of from about 20 to about 1,000 ppmw, in the range of from about 40 to about 500 ppmw, or in the range of from 50 to 200 ppmw.

In one embodiment of the present invention, cobalt and bromine can both be present in the catalyst system. The weight ratio of cobalt to bromine (Co:Br) in the catalyst system can be in the range of from about 0.25:1 to about 4:1, in the range of from about 0.5:1 to about 3:1, or in the range of from 0.75:1 to 2:1. In another embodiment, cobalt and manganese can both be present in the catalyst system. The weight ratio of cobalt to manganese (Co:Mn) in the catalyst system can be in the range of from about 0.3:1 to about 40:1, in the range of from about 5:1 to about 30:1, or in the range of from 10:1 to 25:1.

During oxidation, the ratio of the mass flow rate of the solvent to the mass flow rate of the oxidizable compound (e.g., para-xylene) entering oxidation zone 110 can be maintained in the range of from about 2:1 to about 50:1, in the range of from about 5:1 to about 40:1, or in the range of from 7.5:1 to 25:1.

The predominately gas-phase oxidant stream introduced into oxidation zone 110 can comprise in the range of from about 5 to about 40 mole percent molecular oxygen, in the range of from about 15 to about 30 mole percent molecular oxygen, or in the range of from 18 to 24 mole percent molecular oxygen. The balance of the oxidant stream can be comprised primarily of a gas or gases, such as nitrogen, that are inert to oxidation. In one embodiment, the oxidant stream consists essentially of molecular oxygen and nitrogen. In another embodiment, the oxidant stream can be dry air that comprises about 21 mole percent molecular oxygen and about 78 to about 81 mole percent nitrogen. In an alternative embodiment of the present invention, the oxidant stream can comprise substantially pure oxygen.

During liquid-phase oxidation in oxidation zone 110, the oxidant stream can be introduced into oxidation zone 110 in an amount that provides molecular oxygen somewhat exceeding the stoichiometric oxygen demand. Thus, the ratio of the mass flow rate of the oxidant stream (e.g., air) to the mass flow rate of the oxidizable compound (e.g., para-xylene) entering oxidation zone 110 can be maintained in the range of from about 0.5:1 to about 20:1, in the range of from about 1:1 to about 10:1, or in the range of from 2:1 to 6:1.

The liquid-phase oxidation reaction carried out in oxidation zone 110 can be a precipitating reaction that generates solids. In one embodiment, the liquid-phase oxidation carried out in oxidation zone 110 can cause at least about 10 weight percent of the oxidizable compound (e.g., para-xylene) introduced into oxidation zone 110 to form solids (e.g., crude terephthalic acid ("CTA") particles) in the reaction medium. In another embodiment, the liquid-phase oxidation carried out in oxidation zone 110 can cause at least about 50 weight percent of the oxidizable compound (e.g., para-xylene) introduced into oxidation zone 110 to form solids (e.g., CTA particles) in the reaction medium. In yet another embodiment, the liquid-phase oxidation carried out in oxidation zone 110 can cause at least about 90 weight percent of the oxidizable compound (e.g., para-xylene) introduced into oxidation zone 110 to form solids (e.g., CTA particles) in the reaction medium. In one embodiment, the solids content of the reaction medium can be maintained in the range of from about 1 to about 50 weight percent, in the range of from about 5 to about 40 weight percent, in the range of from about 10 to about 35 weight percent, or in the range of from 15 to 30 weight percent. As used herein, the term "solids content" shall denote the weight percent solids in a multi-phase mixture.

During oxidation in oxidation zone 110, the multi-phase reaction medium can be maintained at an elevated temperature in the range of from about 125 to about 200° C., in the range of from about 150 to about 180° C., or in the range of from 155 to 165° C. The overhead pressure in oxidation zone 110 can be maintained in the range of from about 1 to about 20 bar gauge (barg), in the range of from about 2 to about 12 barg, or in the range of from 4 to 8 barg.

In the embodiment of FIG. 2, a crude slurry can be withdrawn from an outlet of oxidation zone 110 via line 124. The solid phase of the crude slurry in line 124 can be formed primarily of CTA particles. The liquid phase of the crude slurry in line 124 can be a liquid mother liquor comprising at least a portion of the solvent, one or more catalyst components, and minor amounts of dissolved terephthalic acid ("TPA"). In one embodiment, the crude slurry in line 124 can comprise acetic acid in an amount of at least about 10 weight percent. The solids content of the crude slurry in line 124 can be the same as the solids content of the reaction medium in oxidation zone 110, discussed above. In another embodiment, the crude slurry in line 124 can have a solids content of at least about 15 weight percent.

In one embodiment of the present invention, the crude slurry in line 124 can comprise impurities. As used herein, the term "impurities" is defined as any substance other than TPA, solvent, catalyst, and water. Such impurities can include oxidation byproducts formed during the at least partial oxidation of the above-mentioned oxidizable compound (e.g., para-xylene) including, but not limited to, benzoic acid (BA), bromo-benzoic acid, bromo-acetic acid, isophthalic acid, trimellitic acid, 2,5,4'-tricarboxybiphenyl, 2,5,4'-tricarboxybenzophenone, para-toluic acid (p-TAc), 4-carboxybenzaldehyde (4-CBA), monocarboxyfluorenones, monocarboxyfluorenes, dicarboxyfluorenes, and/or dicarboxyfluorenones.

Subsequent to removal from oxidation zone 110, at least a portion of the crude slurry can be introduced into post oxidation zonepost oxidation zone 126 via line 124. In one embodiment, the crude slurry can be treated in post oxidation zonepost oxidation zone 126 such that the concentration of at least one of the above-mentioned impurities in the crude slurry is reduced, thereby producing a purified slurry. Such reduction in the concentration of impurities in the TPA can be accomplished by oxidative digestion, hydrogenation, and/or dissolution/recrystallization.

In one embodiment of the present invention, the crude slurry fed to post oxidation zone 126 can have a 4-CBA content of at least about 100 parts per million based on the weight of the solids in the crude slurry (ppmwcs), in the range of from about 200 to about 10,000 ppmwcs, or in the range of from 800 to 5,000 ppmwcs. The crude slurry fed to post oxidation zonepost oxidation zone 126 can have a p-TAc content of at least about 250 ppmwcs, in the range of from about 300 to about 5,000 ppmwcs, or in the range of from 400 to 1,500 ppmwcs. The purified slurry exiting post oxidation zonepost oxidation zone 126 can have a 4-CBA content of less than about 150 parts per million based on the weight of the solids in the purified slurry (ppmwps), less than about 100 ppmwps, or less than 50 ppmwps. The purified slurry exiting post oxidation zone 126 can have a p-TAc content of less than about 300 ppmwps, less than about 200 ppmwps, or less than 150 ppmwps. In one embodiment, treatment of the crude slurry in post oxidation zone 126 can cause the purified slurry exiting post oxidation zone 126 to have a 4-CBA and/or p-TAc content that is at least about 50 percent less than the 4-CBA and/or p-TAc content of the crude slurry fed to post oxidation zone 126, at least about 85 percent less, or at least 95 percent less. By way of illustration, if the 4-CBA content of the crude slurry fed to post oxidation zone 126 is 200 ppmwcs and the 4-CBA content of the purified slurry exiting post oxidation zone 126 is 100 ppmwps, then the 4-CBA content of the purified slurry is 50 percent less than the 4-CBA content of the crude slurry.

In one embodiment of the present invention, the crude slurry can be subjected to purification by oxidative digestion in post oxidation zone 126. As used herein, the term "oxidative digestion" denotes a process step or steps where a feed comprising solid particles is subjected to oxidation under conditions sufficient to permit oxidation of at least a portion of the impurities originally trapped in the solid particles. Post oxidation zone 126 can comprise one or more reactors or zones. In one embodiment, post oxidation zone 126 can comprise one or more mechanically-agitated reactors. A secondary oxidant stream, which can have the same composition as the gas-phase oxidant stream fed to oxidation zone 110, can be introduced into post oxidation zone 126 to provide the molecular oxygen required for oxidative digestion. Additional oxidation catalyst can be added if necessary. In an alternative embodiment of the present invention, a stream comprising hydrogen can be introduced into post oxidation zone 126 for at least partial hydrogenation of the crude slurry.

When oxidative digestion is employed in post oxidation zone 126, the temperature at which oxidative digestion is carried out can be at least about 10° C. greater than the temperature of oxidation in oxidation zone 110, in the range of from about 20 to about 80° C. greater, or in the range of from 30 to 50° C. greater. The additional heat required for the operation of post oxidation zone 126 can be provided by supplying a vaporized solvent to post oxidation zone 126 and allowing the vaporized solvent to condense therein. The oxidative digestion temperature in post oxidation zone 126 can be maintained in the range of from about 180 to about 240° C., in the range of from about 190 to about 220° C., or in the range of from 200 to 210° C. The oxidative digestion pressure in post oxidation zone 126 can be maintained in the range of from about 100 to about 350 pounds per square inch gauge (psig), in the range of from about 175 to about 275 psig, or in the range of from 185 to 225 psig.

In one embodiment of the present invention, post oxidation zone 126 can include two digestion reactors/zones—an initial digester and a final digester. When post oxidation zone 126 includes an initial digester and a final digester, the final digester can be operated at a lower temperature and pressure than the initial digester. In one embodiment, the operating temperature of the final digester can be at least about 2° C. lower than the operating temperature of the initial digester, or in the range of from about 5 to about 15° C. lower than the operating temperature of the initial digester. In one embodiment, the operating pressure of the final digester can be at least about 5 psig lower than the operating pressure of the initial digester, or in the range of from about 10 to about 50 psig lower than the operating pressure of the initial digester. The operating temperature of the initial digester can be in the range of from about 195 to about 225° C., in the range of from 205 to 215° C., or about 210° C. The operating pressure of the initial digester can be in the range of from about 215 to about 235 psig, or about 225 psig. The operating temperature of the final digester can be in the range of from about 190 to about 220° C., in the range of from 200 to 210° C., or about 205° C. The operating pressure of the final digester can be in the range of from about 190 to 210 psig, or about 200 psig.

In one embodiment of the present invention, post oxidation zone 126 can comprise optional first and second solvent swap zones. Optional first and second solvent swap zones can operate to replace at least a portion of the existing solvent in a slurry with a replacement solvent. Equipment suitable for such replacement includes, but is not limited to, a decanter centrifuge followed by a reslurry with replacement solvent, a disc stack centrifuge, an advancing front crystallizer, or multiple decanter centrifuges with optional counter current washing. The replacement oxidation solvent can have substantially the same composition as the solvent introduced into oxidation zone 110, as described above. Additionally, the replacement oxidation solvent can comprise at least a portion of the acid-containing composition originating from the above-described esterification of lignocellulosic material.

In one embodiment, the crude slurry fed to post oxidation zone 126 can be treated in the optional first solvent swap zone prior to purification of the crude slurry by the above-mentioned oxidative digestion. In another embodiment, a purified slurry resulting from oxidative digestion of the crude slurry can be treated in the optional second solvent swap zone. In one embodiment, at least a portion of the displaced oxidation solvent from the optional first and/or second solvent swap zones can be discharged from post oxidation zone 126 via line 128. At least a portion of the displaced oxidation solvent in line 128 can be routed to purge treatment zone 162 via line 130, and/or oxidation zone 110 via line 132.

In another embodiment of the present invention, post oxidation zone 126 can comprise an optional crystallization zone and/or an optional cooling zone. A purified slurry resulting from the above-mentioned oxidative digestion of the crude slurry can be treated in the optional crystallization zone to at least partially increase the particle size distribution of the purified slurry. Optional crystallization zone can comprise any equipment known in the art that can operate to increase the particle size distribution of the purified slurry. When an optional cooling zone is employed, the purified slurry can be cooled therein to a temperature in the range of from about 20 to about 195° C. When both a crystallization zone and a cooling zone are employed, the purified slurry can be treated first in the crystallization zone and subsequently in the cooling zone.

Referring still to FIG. 2, a purified slurry can be withdrawn from an outlet of post oxidation zone 126 via line 134. The solid phase of the purified slurry can be formed primarily of purified terephthalic acid (PTA) particles, while the liquid phase can be formed of a mother liquor. The solids content of the purified slurry in line 134 can be in the range of from about 1 to about 50 percent by weight, in the range of from about 5 to about 40 weight percent, or in the range of from 20 to 35 weight percent. In one embodiment of the present invention, at least a portion of the purified slurry in line 134 can be employed as an isolation feed slurry which can be introduced into product isolation zone 136.

Product isolation zone 136 can separate the crude slurry and/or the purified slurry into a predominately fluid phase mother liquor and a TPA product wet cake. Product isolation zone 136 can comprise any method of solid/liquid separation known in the art that is capable of generating a wet cake and a mother liquor stream. In addition, it may be desirable for product isolation zone 136 to have the capability of washing the wet cake. Suitable equipment for use in product isolation zone 136 includes, but is not limited to, a pressure drum filter, a vacuum drum filter, a vacuum belt filter, multiple solid bowl centrifuges with optional counter current wash, or a perforated centrifuge.

In one embodiment of the present invention, a wash stream can be introduced into product isolation zone 136 to wash at least a portion of the wet cake generated in product isolation zone 136, thereby producing a washed wet cake. In one embodiment, the wash stream can comprise acetic acid and/or water. Optionally, after washing the wet cake, the used wash liquor can be withdrawn from product isolation zone 136, and at least a portion of the wash liquor can be routed, either directly or indirectly, to oxidation zone 110.

The above-mentioned wet cake generated in product isolation 136 can primarily comprise solid particles of TPA. The solid TPA particles can comprise CTA and/or PTA particles. The wet cake can comprise in the range of from about 5 to about 30 weight percent liquid, in the range of from about 10 to about 25 weight percent liquid, or in the range of from 12 to 23 weight percent liquid. Additionally, the TPA product wet cake can comprise oxidation byproducts, as discussed above. In one embodiment, the TPA product can comprise a cumulative concentration of mono-functional oxidation byproducts of less than about 1,000 ppmw, less than about 750 ppmw, or less than 500 ppmw.

In one embodiment of the present invention, the wet cake produced in product isolation zone 136 can be introduced into a drying zone (not shown) to thereby produce a dry TPA particulate product comprising solid TPA particles. The drying zone can comprise any drying device known in the art that can produce a dried TPA particulate product comprising less than about 5 weight percent liquid, less than about 3 weight percent liquid, or less than 1 weight percent liquid.

In another embodiment, the wet cake produced in product isolation zone 136 can be introduced into a solvent swap zone (not shown) to produce a wet TPA particulate product comprising solid TPA particles. The solvent swap zone can operate to replace at least a portion of the liquid in the wet cake with a replacement solvent. Equipment suitable for such replacement includes, but is not limited to, a decanter centrifuge followed by a reslurry with replacement solvent, a disc stack centrifuge, an advancing front crystallizer, or multiple decanter centrifuges with counter current washing. The wet TPA particulate product can comprise in the range of from about 5 to about 30 weight percent liquid, in the range of from about 10 to about 25 weight percent liquid, or in the range of from 12 to 23 weight percent liquid.

Referring still to FIG. 2, the above-mentioned mother liquor can be discharged from product isolation zone 136 via line 138. In one embodiment of the present invention, at least a portion of the mother liquor in line 138 can optionally be introduced into a solids removal zone (not shown). A solids removal zone can comprise any equipment known in the art that is operable to remove a sufficient amount of solids from the mother liquor to produce a solids-depleted mother liquor comprising less than about 5 weight percent solids, less than about 2 weight percent solids, or less than 1 weight percent solids. Suitable equipment that may be employed in a solids removal zone includes a pressure filter, such as, for example, a filter press, a candle filter, a pressure leaf filter, and/or a cartridge filter.

In one embodiment of the present invention, at least a portion of the optionally solids-depleted mother liquor in line 138 can be withdrawn from line 138 via line 140 to form a purge feed stream. The amount of mother liquor withdrawn by line 140 to form the purge feed stream can be in the range of from about 1 to about 55 percent of the total weight of the mother liquor, in the range of from about 5 to about 45 percent by weight, or in the range of from 10 to 35 percent by weight. Optionally, at least a portion of the displaced oxidation solvent discharged from post oxidation zone 126 in line 130 can be combined with the purge feed stream and introduced into purge treatment zone 162 substantially simultaneously. In another embodiment, at least a portion of the remaining mother liquor in line 138 can be routed, either directly or indirectly, to oxidation zone 110 via line 142. Optionally, at least a portion of the wash liquor in line 144 discharged from product isolation zone 136 can be combined with at least a portion of the mother liquor in line 142 prior to introduction into oxidation zone 110.

In one embodiment of the present invention, the mother liquor in line 138, and consequently the purge feed stream in line 140, can comprise solvent, one or more catalyst components, oxidation byproducts, and TPA. The solvent in the mother liquor in line 138 and the purge feed stream in line 140 can comprise a monocarboxylic acid. In one embodiment, the solvent can comprise water and/or acetic acid. The mother liquor in line 138 and the purge feed stream in line 140 can comprise solvent in an amount of at least about 85 weight percent, at least about 95 weight percent, or at least 99 weight percent.

The catalyst components in the mother liquor in line 138 and the purge feed stream in line 140 can comprise the catalyst components as described above with reference to the catalyst system introduced into oxidation zone 110 (e.g., cobalt, manganese, and/or bromine). The mother liquor in line 138 and the purge feed stream in line 140 can have a cumulative concentration of all of the catalyst components in the range of from about 500 to about 20,000 ppmw, in the range of from about 1,000 to about 15,000 ppmw, or in the range of from 1,500 to 10,000 ppmw.

The oxidation byproducts in the mother liquor in line 138 and the purge feed stream in line 140 can comprise one or more of the oxidation byproducts discussed above. In one embodiment, the oxidation byproducts in the mother liquor in line 138 and the purge feed stream in line 140 can comprise both BA and non-BA byproducts. As used herein, the term "non-BA byproducts" is defined as any oxidation byproduct that is not benzoic acid. Non-BA byproducts include, but are not limited to, isophthalic acid (IPA), phthalic acid (PA), trimellitic acid, 2,5,4'-tricarboxybiphenyl, 2,5,4'-tricarboxybenzophenone, p-TAI, 4-CBA, naphthalene dicarboxylic acid, monocarboxyfluorenones, monocarboxyfluorenes, dicarboxyfluorenes, and/or dicarboxyfluorenones. In one embodiment, the mother liquor in line 138 and the purge feed stream in line 140 can comprise BA in an amount in the range of from about 500 to about 150,000 ppmw based on the weight of the purge feed stream, in the range of from about 1,000 to about 100,000 ppmw, or in the range of from 2,000 to 50,000 ppmw. Additionally, the mother liquor in line 138 and the purge feed stream in line 140 can have a cumulative concentration of non-BA byproducts in the range of from about 500 to about 50,000 ppmw, in the range of from about 1,000 to about 20,000 ppmw, or in the range of from 2,000 to 10,000 ppmw.

In one embodiment of the present invention, the mother liquor in line 138 and the purge feed stream in line 140 can comprise solids in an amount of less than about 5 weight percent, less than about 2 weight percent, or less than 1 weight percent. Additionally, the purge feed stream can have a temperature of less than about 240° C., in the range of from about 20 to about 200° C., or in the range of from 50 to 100° C.

Referring still to FIG. 2, the purge feed stream can be introduced into purge treatment zone 162 via line 140. Purge treatment zone 162 can separate the purge feed stream into a catalyst rich stream and a purge stream. The catalyst rich stream can be discharged from purge treatment zone 162 via line 150, and the purge stream can be discharged via line 146.

The catalyst rich stream in line 150 can have a relatively higher cumulative concentration of all of the catalyst components on a weight basis compared to the cumulative concentration of all of the catalyst components in the purge feed stream in line 140. In one embodiment of the present invention, the catalyst rich stream in line 150 can have a cumulative concentration of all of the catalyst components that is at least about 1.5 times the cumulative concentration of all of the catalyst components in the purge feed stream on a weight basis, at least about 5 times the cumulative concentration of all of the catalyst components in the purge feed stream on a weight basis, or at least 10 times the cumulative concentration of all of the catalyst components in the purge feed stream on a weight basis. Depending of the temperature and pressure of the catalyst rich stream upon exiting purge treatment zone 162, the catalyst rich stream in line 150 can predominately comprise solids or fluid. Thus, in one embodiment, the catalyst rich stream in line 150 can comprise at least about 50 weight percent fluid, at least about 70 weight percent fluid, or at least 90 weight percent fluid. In an alternate embodiment, the catalyst rich stream in line 150 can comprise at least about 50 weight percent solids, at least about 70 weight percent solids, or at least 90 weight percent solids.

In one embodiment of the present invention, at least a portion of the catalyst rich stream in line 150 can be routed, either directly or indirectly, to oxidation zone 110, where at least about 50 weight percent, at least about 60 weight percent, or at least 70 weight percent of the catalyst components of the catalyst rich stream are introduced into oxidization zone 110. In one embodiment, prior to routing, a liquid can optionally be added to the catalyst rich stream in line 150 to produce a reslurried catalyst rich stream. The optional reslurried catalyst rich stream can comprise at least about 35 weight percent liquid, at least about 50 weight percent liquid, or at least 65 weight percent liquid. The liquid added to the catalyst rich stream can be, for example, acetic acid and/or water.

It will be understood by one skilled in the art that each of the above-described embodiments, as well as any sub-parts of those embodiments, may be operated in a continuous or a non-continuous manner. Non-continuous operations include, but are not limited to, batch-wise operations, cyclical operations, and/or intermittent operations. In some of the embodiments above, temperature ranges are provided for a specified operation. For each of the above embodiments where a temperature range is provided, the temperature is defined as the average temperature of the substance in the given zone or section.

EXAMPLES

This invention can be further illustrated by the following examples of embodiments thereof, although it will be understood that these examples are included merely for the purposes of illustration and are not intended to limit the scope of the invention unless otherwise specifically indicated.

In Examples 1 and 2, glacial acetic acid and acetic acid recovered from wood process respectively, water (5.0 wt. %) and the catalyst components in concentrations of 2400 ppmw Co, 90 ppmw Mn and 1750 ppmw Br were transferred to a 300 mL titanium autoclave equipped with a high pressure condenser, a baffle an Isco pump and a cold trap after the condenser. Cobalt, manganese and ionic bromine were provided as cobalt (II) acetate tetrahydrate, manganese (II) acetate and aqueous hydrobromic acid respectively. The autoclave was pressurized with approximately 50 psig of nitrogen and the homogeneous mixture was heated to the desired temperature in a closed system (i.e., with no gas flow) with stirring. At reaction temperature, 160° C., an air flow of 1500 sccm was introduced at the bottom of the solution and the reaction pressure was adjusted to the desired pressure, 180 psig. Para-xylene was fed to the mixture at a rate of 0.28 mL/min via a high pressure Isco pump (this is t=0 for the reaction time). After 30 seconds from the start of substrate feeding, 1.0 g of peracetic acid in 5.0 mL of acetic acid was introduced using a blow-case to start the reaction. The feed was stopped after 1 h and the reaction continued for an additional hour at the same conditions of air flow, temperature and pressure. After the reaction time was completed, the air flow was stopped and the autoclave was cooled to room temperature and depressurized. The heterogeneous mixture was filtered to isolate the crude terephthalic acid (CTA). The mass of the filtrate was recorded. The CTA was washed with 25 mL of acetic acid (96%) two times and then twice with 25 mL of DI water. The washed CTA was dried at 110° C. under vacuum overnight and then weighed. The solids, the filtrates and liquid sample from the trap were analyzed by liquid chromatography (LC) method. See Tables 2, 3 and 4 for results. The acetylated wood acetic acid before use for oxidation, the filtrate and the liquid sample from the trap were also analyzed by Gas Chromatographic Mass Selective Method. See FIG. 3 and summary Table 1.

The Off-gas was analyzed for CO and $CO_2$ by ND-IR (ABB, Advanced Optima) and $O_2$ by a paramagnetism detection system (Servomex, 1440 Model).

TABLE 1

Wood impurities analysis before and after oxidation using Mass Selective GC/MS technique.

| Acetylated-wood acid species | Acetylated-wood acid before oxidation (ppm) | Filtrate sample (ppm) | Sample in the trap (ppm) |
|---|---|---|---|
| alpha-Pinene | 35.6 | NA (BD) | NA (BD) |
| Camphene | 43 | NA (BD) | NA (BD) |
| Limonene | 164.3 | NA (BD) | NA (BD) |
| p-Cymene | 30.8 | NA (BD) | NA (BD) |
| gamma-Terpinene | 9.12 | NA (BD) | NA (BD) |
| Terpinolene | 33 | NA (BD) | NA (BD) |
| isobornyl acetate* | 0.99 | 0.237 (both peaks) 0.04 (one peak) | 0.201 (both peaks) 0.03 (one peak) |

*Possible isomer peak was detected.

TABLE 2

LC results for the solids using semi-batch reactions performed as described above.

| Analysis | Components | Result (ppmw). Control experiment (Example 1) | Result (ppmw). Using acetic acid from wood treatment (Example 2) |
|---|---|---|---|
| LC27 | 2,6-Dicarboxy Anthraquinone | 18.1 | 5 |
| | 2,6-Dicarboxy Fluorenone | 4.5 | 1 |
| | 2,7-Dicarboxy Fluorenone | 0 | 0 |
| | 4,4-Dicarboxy Benzophenone | 24 | 3.1 |
| | 4,4-Dicarboxy Biphenyl index | 2.1 | 2 |
| | 4,4-Dicarboxy Stilbene | 37.8 | 13 |
| | 4-Bromo Benzoic Acid | 7.7 | 9 |
| | Mono Carboxy Fluorenone | 0 | 0 |
| | Tricarboxy Benzophenone | 31.4 | 3 |
| | Tricarboxy Biphenyl | 8 | 4 |
| LC28 | 4-Carboxybenzaldehyde | 1918.1 | 1916.8 |
| | Benzoic Acid | 0 | 0 |
| | Hydroxybenzoic Acid (HBA) | 0 | 0 |
| | Hydroxymethyl Benzoic Acid (HMBA) | 12.8 | 13 |
| | Isophthalic Acid (IPA) | 10.2 | 7.7 |
| | Phthalic acid | 0 | 0 |
| | Trimellitic Acid (TMA) | 66.8 | 18.9 |
| | p-Tolualdehyde | 42.4 | 37.1 |
| | p-Toluic Acid | 402.7 | 326.1 |

TABLE 3

LC results for the filtrates using semi-batch reactions performed as described above.

| Analysis | Components | Result (ppmw). Control experiment (Example 1) | Result (ppmw). Using acetic acid from wood treatment (Example 2) |
|---|---|---|---|
| LC27 | 2,6-Dicarboxy Anthraquinone | 6.5 | 0.00 |
| | 2,6-Dicarboxy Fluorenone | 1.8 | 0.00 |
| | 2,7-Dicarboxy Fluorenone | 0 | 0.00 |
| | 4,4-Dicarboxy Benzophenone | 122.9 | 8.00 |
| | 4,4-Dicarboxy Biphenyl index | 6.2 | 0.00 |
| | 4,4-Dicarboxy Stilbene | 0 | 0.00 |
| | 4-Bromo Benzoic Acid | 8.3 | 5.00 |
| | Mono Carboxy Fluorenone | 0 | 0.00 |
| | Tricarboxy Benzophenone | 209.4 | 11.00 |
| | Tricarboxy Biphenyl | 5.9 | 3.00 |
| LC28 | 4-Carboxybenzaldehyde | 18.5 | 35 |
| | Benzoic Acid | 262.6 | 58.6 |
| | Hydroxybenzoic Acid (HBA) | 0 | 0 |
| | Hydroxymethyl Benzoic Acid (HMBA) | 2.2 | 0 |
| | Isophthalic Acid (IPA) | 240.7 | 129.1 |
| | Phthalic acid | 71.5 | 38.8 |
| | Terephthalic Acid (TPA) | 284.7 | 131.9 |
| | Trimellitic Acid (TMA) | 110.9 | 26.4 |
| | p-Tolualdehyde | 47.9 | 33.2 |
| | p-Toluic Acid | 68.1 | 89.2 |

TABLE 4

LC results for the sample for the trap using semi-batch reactions performed as described above.

| Analysis | Components | Result (ppmw). Using acetic acid from wood treatment (Example 2) |
|---|---|---|
| LC27 | 2,6-Dicarboxy Anthraquinone | 0.00 |
| | 2,6-Dicarboxy Fluorenone | 0.00 |
| | 2,7-Dicarboxy Fluorenone | 0.00 |
| | 4,4-Dicarboxy Benzophenone | 0.00 |
| | 4,4-Dicarboxy Biphenyl index | 0.00 |
| | 4,4-Dicarboxy Stilbene | 0.00 |
| | 4-Bromo Benzoic Acid | 0.00 |
| | Mono Carboxy Fluorenone | 0.00 |
| | Tricarboxy Benzophenone | 0.00 |
| | Tricarboxy Biphenyl | 0.00 |
| LC28 | 4-Carboxybenzaldehyde | 0 |
| | Benzoic Acid | 10.2 |
| | Hydroxybenzoic Acid (HBA) | 0 |
| | Hydroxymethyl Benzoic Acid (HMBA) | 0 |
| | Isophthalic Acid (IPA) | 0 |
| | Phthalic acid | 0 |
| | Terephthalic Acid (TPA) | 44.7 |
| | Trimellitic Acid (TMA) | 0 |
| | p-Tolualdehyde | 0 |
| | p-Toluic Acid | 0 |

Analytical

Quantitative Determination of Binuclear Impurities in Terephthalic Acid Solids and Filtrates by Liquid Chromatography Using Mass Spectrometric Detection [LC-27]:

Samples are analyzed with an Agilent 1100 LC unit consisting of a quaternary pump, an autosampler (5 uL injection), and a thermostated column compartment (45° C.). Mass selective detection (MSD) is accomplished with a Waters model ZQ mass spectrometer operating in the electrospray negative mode (ESI−). [Specific MS operating conditions include: capillary voltage, 3.0 KV; cone voltage, 25 or 40V;

extractor voltage, 3.0V; RF lens voltage, 0.5V; desolvation temperature, 450° C.; source temperature, 130° C.; desolvation flow, 750 L/hr]. The chromatograph is fitted with a 150 mm×4.6 mm Waters Spherisorb S3 ODS2 C18 column packed with 3 micron particles. The solvent flow program is shown in the table below: Channel A is 1.5% acetic acid in water, channel B is tetrahydrofuran (THF), and channel C is acetonitrile (ACN)

| Time (min) | % A  | % B  | % C  | Flow (ml/min) |
|------------|------|------|------|---------------|
| Initial    | 84.0 | 16.0 | 0.0  | 0.90          |
| 18.3       | 54.0 | 16.0 | 30.0 | 0.90          |
| 19.9       | 24.0 | 16.0 | 60.0 | 0.90          |
| 21.6       | 24.0 | 16.0 | 60.0 | 0.90          |
| 22.4       | 84.0 | 16.0 | 0.0  | 0.90          |
| 30         | 84.0 | 16.0 | 0.0  | 0.90          |

Waters Masslynx software is used for control of the LC and the MSD. Waters Quanlynx software is used for calibration and data processing. A 4 point (including the origin) quadratic calibration fit is used for the quantification of each analyte with mono carboxy anthraquinone (MCA) serving as the internal standard. Samples are prepared by dissolving ~0.10 g (weighed accurately to 0.0001 g) in 10 ml of 50:50 DMSO/acetonitrile solution containing the MCA internal standard. Sonication is used to ensure complete dissolution of the sample in the solvent. A portion of the prepared sample is transferred to an autosampler vial for injection onto the LC.

Quantitative Determination of Eight Monocyclic Selected Impurities in Terephthalic Acid Solids and Filtrates by Liquid Chromatography With a Diode Array Detector [LC-28]:

Samples are analyzed with an Agilent 1200 series LC unit consisting of a quaternary pump, an autosampler (5 uL injection), a thermostated column compartment (30° C.) and a diode array UV/vis detector (240 nm). The chromatograph is fitted with two (2) 150 mm×4.6 mm Waters Spherisorb ODS2 columns (3 micron particles) in series. The solvent flow program is shown in the table below: Channel A is 0.1% phosphoric acid in water, channel B is acetonitrile, and channel C is tetrahydrofuran (THF)

| Time (min) | % A  | % B  | % C  | Flow (ml/min) |
|------------|------|------|------|---------------|
| Initial    | 79.0 | 0.0  | 21.0 | 0.90          |
| 20         | 79.0 | 0.0  | 21.0 | 0.90          |
| 38         | 34.0 | 45.0 | 21.0 | 1.00          |
| 38.5       | 14.0 | 65.0 | 21.0 | 1.00          |
| 39.5       | 14.0 | 65.0 | 21.0 | 1.00          |
| 40         | 79.0 | 0.0  | 21.0 | 1.10          |
| 41         | 79.0 | 0.0  | 21.0 | 1.30          |
| 44         | 79.0 | 0.0  | 21.0 | 0.90          |
| 46         | 79.0 | 0.0  | 21.0 | 0.90          |

EZChrom elite is used for control of the HPLC and for data processing. A 3 point linear calibration is used for the quantification of individual analytes. Samples are prepared by dissolving ~0.20 g of TPA solid or 0.10 g of TPA filtrate (weighed accurately to 0.0001 g) in 10 ml of 50:50 DMF/THF. Sonication is used to ensure complete dissolution of the sample in the solvent. A portion of the prepared sample is transferred to an autosampler vial for injection onto the LC.

Gas Chromatographic Mass Selective Method 1—

Samples were analyzed using a Thermo Scientific DSQ Single Quad Mass Spectrometer with Trace Ultra Gas Chromatograph and a Tri-Plus Autosampler for liquid injections (or equivalent). The gas chromatograph was equipped with a split/heated injector (250° C.) and a capillary column (30 meter×0.25 mm ID) coated with (50% phenyl)-methylpolysiloxane at 0.25 mm film thickness (such as DB-17 equivalent). Helium was used as the carrier gas at a constant flow of 1.5 mL/minute, calculated and programmed within the gas chromatograph. The column temperature was programmed as follows: The initial oven temperature was set at 40° C. and held for 1 minute, the oven was ramped up to 150° C. at 6° C./minute and was held at 150° C. for 5 minutes, then the oven was ramped up to 300° C. at 20° C./minute and was held at 300° C. for 5 minutes (the total run time was 36 minutes). 1.0 μL of the prepared sample solution was injected with a split ratio of 7:1. Thermo Xcalibur Quant data system software was used for data acquisition and processing. The single quad mass spectrometer was set with a source temperature of 250° C., a gain of 3, and a MS transfer line temperature of 280° C. An internal standard solution was prepared by dissolving 1 uL of p-dichlorobenzene in 1.0 mL of glacial acetic acid. Samples were prepared by pipetting 1.0 mL of each sample into a vial, to which 3 μL of the internal standard solution was added with a syringe (701N Hamilton, or equivalent). The Thermo DSQ mass spectrometer was set to monitor selected/specific masses: m/z=91 (p-Cymene), m/z=93 (dl-Limonene, γ-Terpinene, and Terpinolene), m/z=136 (α-Pinene, Camphene), and m/z=146 (p-Dichlorobenzene). Positive identifications in samples of interest were made using selective mass detection, as well as retention time comparison with known standards.

Calibration standards were prepared using reference material purchased from Aldrich (at 95% purity or better) in the following way: A stock solution was prepared by adding 0.0244 g γ-Terpinene, 0.0216 g α-Pinene, 0.0231 g p-Cymene, 0.0259 g Terpinolene, 0.0259 g Isobornyl Acetate, 0.0264 g dl-Limonene, and 0.0266 g Camphene to a 100 mL volumetric flask where the volume was brought to 100 mL with glacial acetic acid. Five calibration standards were prepared, See Table 5.

Standard 5 was prepared by diluting 1.0 mL of the stock solution into 25 mL of glacial acetic acid, volumetrically. 1.0 mL of Standard 5 was placed in a vial, to which 3.0 uL of the internal standard solution was added.

Standard 4 was prepared by diluting 1.0 mL of the stock solution into 50 mL of glacial acetic acid, volumetrically. 1.0 mL of Standard 4 was placed in a vial, to which 3.0 uL of the internal standard solution was added.

Standard 3 was prepared by diluting 1.0 mL of the stock solution into 100 mL of glacial acetic acid, volumetrically. 1.0 mL of Standard 3 was placed in a vial, to which 3.0 uL of the internal standard solution was added.

Standard 2 was prepared by diluting 0.5 mL of the stock solution into 100 mL of glacial acetic acid, volumetrically. 1.0 mL of Standard 2 was placed in a vial, to which 3.0 uL of the internal standard solution was added.

Standard 1 was prepared by diluting 1.0 mL of Standard 3 into 10 mL of glacial acetic acid, volumetrically. 1.0 mL of Standard 1 was placed in a vial, to which 3.0 uL of the internal standard solution was added.

These five calibration standards (with internal standard added) were used in the approximate range of 0.2 ppm to 11 ppm each of γ-Terpinene, α-Pinene, p-Cymene, Terpinolene, dl-Limonene, Isobornyl acetate, and Camphene to make a 5 point linear calibration for each compound. The resulting linear calibration equation was calculated by the Xcalibur software and used by the data system to determine quantitative results in samples of interest.

TABLE 5

Calibration standards for Gas Chromatographic Mass Selective Method 1.

| Component | Weight/100 mL Stock Solution | 1:1000 diktion (1:10 dilution of standard 3) Standard 1 | 0.5 mL stock/100 mL Standard 2 | 1 mL stock/100 mL Standard 3 | 1 mL stock/50 mL Standard 4 | 1 mL stock/25 mL Standard 5 |
|---|---|---|---|---|---|---|
| a-Terpinene | 0.0244 g | 0.24 ppm | 1.2 ppm | 2.4 ppm | 4.9 ppm | 9.8 ppm |
| a-Pinene | 0.0216 g | 0.22 ppm | 1.1 ppm | 2.2 ppm | 4.3 ppm | 8.6 ppm |
| p-Cymene | 0.0231 g | 0.23 ppm | 1.2 ppm | 2.3 ppm | 4.6 ppm | 9.2 ppm |
| Terpinolene | 0.0259 g | 0.26 ppm | 1.3 ppm | 2.6 ppm | 5.2 ppm | 10.4 ppm |
| Isobornyl Acetate | 0.0259 g | 0.26 ppm | 1.3 ppm | 2.6 ppm | 5.2 ppm | 10.4 ppm |
| D-Limonene | 0.0264 g | 0.26 ppm | 1.3 ppm | 2.6 ppm | 5.3 ppm | 10.6 ppm |
| Camphene | 0.0266 g | 0.27 ppm | 1.3 ppm | 2.7 ppm | 5.3 ppm | 10.6 ppm |

Gas Chromatographic Mass Selective Method 2 (Isobornyl Acetate Analysis)—

Samples were analyzed using a Thermo Scientific DSQ Single Quad Mass Spectrometer with Trace Ultra Gas Chromatograph and a Tri-Plus Autosampler for liquid injections (or equivalent). The gas chromatograph was equipped with a split/heated injector (250° C.) and a capillary column (30 meter×0.25 mm ID) coated with polyethylene glycol at 0.25 mm film thickness (such as DB-WAX equivalent). Helium was used as the carrier gas at a constant flow of 1.5 mL/minute, calculated and programmed within the gas chromatograph. The column temperature was programmed as follows: The initial oven temperature was set at 40° C. and held for 1 minute, the oven was ramped up to 150° C. at 8° C./minute and was held at 150° C. for 2 minutes, then the oven was ramped up to 240° C. at 20° C./minute and was held at 240° C. for 10 minutes (the total run time was 31 minutes). 1.0 µL of the prepared sample solution was injected with a split ratio of 7:1. Thermo Xcalibur Quant data system software was used for data acquisition and processing. The single quad mass spectrometer was set with a source temperature of 250° C., a gain of 3, and a MS transfer line temperature of 280° C. An internal standard solution was prepared by dissolving 1 uL of p-dichlorobenzene in 1.0 mL of glacial acetic acid. Samples were prepared by pipetting 1.0 mL of each sample into a vial, to which 3 µL of the internal standard solution was added with a syringe (701N Hamilton, or equivalent). The Thermo DSQ mass spectrometer was set to monitor selected/specific masses: m/z=95 (Isobornyl Acetate), and m/z=146 (p-Dichlorobenzene). Positive identifications in samples of interest were made using selective mass detection, as well as retention time comparison with known standards.

Calibration standards were prepared using reference material purchased from Aldrich (at 95% purity or better) in the following way: A stock solution was prepared by adding 0.0259 g Isobornyl Acetate to a 100 mL volumetric flask where the volume was brought to 100 mL with glacial acetic acid. Five calibration standards were prepared, See Table 6.

Standard 5 was prepared by diluting 1.0 mL of the stock solution into 25 mL of glacial acetic acid, volumetrically. 1.0 mL of Standard 5 was placed in a vial, to which 3.0 uL of the internal standard solution was added.

Standard 4 was prepared by diluting 1.0 mL of the stock solution into 50 mL of glacial acetic acid, volumetrically. 1.0 mL of Standard 4 was placed in a vial, to which 3.0 uL of the internal standard solution was added.

Standard 3 was prepared by diluting 1.0 mL of the stock solution into 100 mL of glacial acetic acid, volumetrically. 1.0 mL of Standard 3 was placed in a vial, to which 3.0 uL of the internal standard solution was added.

Standard 2 was prepared by diluting 0.5 mL of the stock solution into 100 mL of glacial acetic acid, volumetrically. 1.0 mL of Standard 2 was placed in a vial, to which 3.0 uL of the internal standard solution was added.

Standard 1 was prepared by diluting 1.0 mL of Standard 3 into 10 mL of glacial acetic acid, volumetrically. 1.0 mL of Standard 1 was placed in a vial, to which 3.0 uL of the internal standard solution was added.

These five calibration standards (with internal standard added) were used in the approximate range of 0.2 ppm to 11 ppm of Isobornyl acetate to make a 5 point linear calibration for each compound. The resulting linear calibration equation was calculated by the Xcalibur software and used by the data system to determine quantitative results in samples of interest.

TABLE 6

Calibration standards for Gas Chromatographic Mass Selective Method 2.

| Component | Weight/100 mL Stock Solution | 1:1000 dilution (1:10 dilution of standard 3) Standard 1 | 0.5 mL stock/100 mL Standard 2 | 1 mL stock/100 mL Standard 3 | 1 mL stock/50 mL Standard 4 | 1 mL stock/25 mL Standard 5 |
|---|---|---|---|---|---|---|
| Isobornyl Acetate | 0.0259 g | 0.26 ppm | 1.3 ppm | 2.6 ppm | 5.2 ppm | 10.4 ppm |

Numerical Ranges

The present description uses numerical ranges to quantify certain parameters relating to the invention. It should be understood that when numerical ranges are provided, such ranges are to be construed as providing literal support for claim limitations that only recite the lower value of the range as well as claims limitation that only recite the upper value of the range. For example, a disclosed numerical range of 10 to 100 provides literal support for a claim reciting "greater than 10" (with no upper bounds) and a claim reciting "less than 100" (with no lower bounds).

DEFINITIONS

As used herein, the terms "a," "an," "the," and "said" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "containing," "contains," and "contain" have the same open-ended meaning as "comprising," "comprises," and "comprise" provided above.

As used herein, the terms "having," "has," and "have" have the same open-ended meaning as "comprising," "comprises," and "comprise" provided above.

As used herein, the terms "including," "includes," and "include" have the same open-ended meaning as "comprising," "comprises," and "comprise" provided above.

CLAIMS NOT LIMITED TO THE DISCLOSED EMBODIMENTS

The preferred forms of the invention described above are to be used as illustration only, and should not be used in a limiting sense to interpret the scope of the present invention. Modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. A process for producing an aromatic carboxylic acid, said process comprising oxidizing an oxidation feed comprising at least one oxidizable compound and at least one solvent comprising a monocarboxylic acid, wherein at least a portion of said monocarboxylic acid originated from a wood acetylation process; and wherein said solvent further comprises one or more terpenes or terpene derivatives; wherein at least 50% of the said terpenes or terpenes derivatives are oxidized in said oxidation reactor to form carbon monoxide and carbon dioxide.

2. The process of claim 1, wherein said solvent further comprises acetic anhydride in an amount of at least 0.01 weight percent based on the weight of monocarboxylic acid employed from said wood acetylation process.

3. The process of claim 2, wherein said oxidizing produces water as a byproduct, wherein at least a portion of said acetic anhydride consumes at least a portion of said water.

4. The process of claim 1, wherein said monocarboxylic acid comprises acetic acid, wherein at least 5 weight percent of said acetic acid is acetic acid originated from said wood acetylation process.

5. The process of claim 4, wherein said solvent comprises a combined concentration of all of said terpenes in an amount of at least 0.01 weight percent based on the weight of acetic acid employed from said wood acetylation process.

6. The process of claim 1, said process further comprising at least one purification step.

7. The process of claim 1, wherein said oxidizable compound comprises para-xylene, wherein said carboxylic acid comprises terephthalic acid.

8. A process for producing an aromatic carboxylic acid, said process comprising:
   (a) contacting at least one lignocellulosic material with a compound containing at least one acetyl group to thereby produce an acetylated lignocellulosic material and an acid-containing composition; and
   (b) introducing at least a portion of said acid-containing composition and an oxidizable compound into a carboxylic acid production process, wherein said acid-containing composition comprises acetic acid; and wherein said acid-containing composition comprises one or more terpenes or terpene derivatives in an amount of at least 0.01 weight percent based on the weight of said acetic acid in said acid-containing composition; wherein at least 50% of the said terpenes or terpenes derivatives are oxidized in said oxidation reactor to form carbon monoxide and carbon dioxide.

9. The process of claim 8, wherein said acid-containing composition further comprises acetic anhydride in an amount of at least 0.01 weight percent based on the weight of said acetic acid in said acid-containing composition.

10. The process of claim 8, wherein said carboxylic acid production process comprises an oxidation reactor, wherein said process further comprises oxidizing at least a portion of said oxidizable compound in the presence of at least a portion of said acid-containing composition in said oxidation reactor, wherein said oxidizing produces water as a byproduct, wherein at least a portion of said acetic anhydride consumes at least a portion of said water.

11. The process of claim 8, wherein said lignocellulosic material comprises wood, wherein said compound containing at least one acetyl group comprises acetic anhydride in an amount of at least 0.05 weight percent.

12. The process of claim 8, wherein said oxidizable compound comprises para-xylene, wherein said carboxylic acid comprises terephthalic acid.

13. The process of claim 10, wherein said carboxylic acid production process further comprises at least one purification step.

14. A process for producing an aromatic carboxylic acid, said process comprising oxidizing an oxidizable compound in an oxidation reactor in the presence of at least one solvent, wherein said solvent comprises acetic anhydride in an amount of at least 0.01 weight percent based on the total weight of the solvent; wherein said solvent comprises acetic anhydride in an amount of at least 0.05 weight percent based on the total weight of the solvent.

15. The process of claim 14, wherein said solvent comprises terpenes in a cumulative amount of at least 0.01 weight percent based on the total weight of the solvent.

16. The process of claim 15, wherein at least a portion of said terpenes or terpenes derivatives are oxidized in said oxidation reactor to form carbon monoxide and carbon dioxide.

17. The process of claim 15, wherein at least 70% of the said terpenes or terpenes derivatives are oxidized in said oxidation reactor to form carbon monoxide and carbon dioxide.

18. The process of claim 15, wherein at least 90% of the said terpenes or terpenes derivatives are oxidized in said oxidation reactor to form carbon monoxide and carbon dioxide.

19. The process of claim 15, wherein at least 99% of the said terpenes or terpenes derivatives are oxidized in said oxidation reactor to form carbon monoxide and carbon dioxide.

20. The process of claim 15, wherein at least 99.9% of the said terpenes or terpenes derivatives are oxidized in said oxidation reactor to form carbon monoxide and carbon dioxide.

21. The process of claim 15, wherein at least a portion of said terpenes or terpenes derivatives are oxidized in said oxidation reactor but do not affect conversion, yield and product quality.

22. The process of claim 14, wherein said oxidizing produces water as a byproduct, wherein at least a portion of said acetic anhydride consumes at least a portion of said water.

23. The process of claim 14, wherein at least a portion of said solvent originates from a wood acetylation process.

24. The process of claim 14, wherein said solvent further comprises acetic acid and/or water, wherein said carboxylic acid comprises terephthalic acid, wherein said oxidizable compound comprises para-xylene.

25. The process of claim 14, said process further comprising at least one purification step.

\* \* \* \* \*